United States Patent [19]

Burough

[11] 4,200,791

[45] Apr. 29, 1980

[54] GAS ANALYZER AND GAS ANALYZING METHOD

[75] Inventor: Irvin G. Burough, Walnut Creek, Calif.

[73] Assignee: Andros Incorporated, Berkeley, Calif.

[21] Appl. No.: 950,327

[22] Filed: Oct. 11, 1978

[51] Int. Cl.² .............................................. G01J 1/00
[52] U.S. Cl. .................................................... 250/343
[58] Field of Search ...................... 250/343, 344, 345; 356/51, 418

[56] References Cited

U.S. PATENT DOCUMENTS

| | | | |
|---|---|---|---|
| 3,926,522 | 12/1975 | Andreotti | 356/418 |
| 3,953,734 | 4/1976 | Dimeff | 250/343 |
| 4,013,260 | 3/1977 | McClatchie et al. | 250/343 |

*Primary Examiner*—Alfred E. Smith
*Assistant Examiner*—Janice A. Howell
*Attorney, Agent, or Firm*—Fitch, Even & Tabin

[57] ABSTRACT

A gas analyzer and gas analyzing method are described of the non-dispersive infrared type wherein infrared energy is passed through a sample cell containing an unknown mixture of gas. The infrared energy passing through the cell is received by a detector and an electrical signal is produced representative thereof. A rotary filter wheel positions at least one filter in the path of the infrared energy, resulting in a pulsating detector output. The electrical signal is processed to produce an output indicating the concentration of the constituents of the gas mixture in the sample cell. Synchronization with the processed electrical signal is obtained by deriving synchronizing pulses directly from the electrical signal produced by the detector.

9 Claims, 3 Drawing Figures

GAS ANALYZER AND GAS ANALYZING METHOD

This invention relates generally to gas analyzers of the non-dispersive infrared type. More particularly, the invention relates to an improved gas analyzer and gas analyzing method wherein synchronizing signals for the signal processing electronics are obtained directly from the detected infrared energy.

Non-dispersive infrared gas analyzers typically utilize an infrared source to produce and direct infrared energy through an unknown gas mixture contained in a sample cell. The energy passing through the sample cell is detected and electrical signals are produced representative thereof. These signals are processed to produce an output indicating the concentration of one or more of the constituents of the gas in the sample cell.

Such gas analyzers utilize the principle that various gases exhibit substantially increased absorption characteristics at specific wavelengths in the infrared radiation spectrum. A gas analyzer of this type is shown and described in U.S. Pat. No. 4,013,260, McClatchie et al, issued Mar. 22, 1977, and assigned to the assignee of the present invention. Another type of non-dispersive infrared gas analyzer is shown and described in U.S. Pat. No. 3,953,734, Dimeff, issued Apr. 27, 1976, and assigned to the United States of America.

In both of the above cited patents, and in similar types of infrared gas analyzers, the beam of infrared energy passing through the sample cell containing the unknown gas mixture is varied by the interposition of one or more filters in the path of the light beam. Typically, each filter represents the wavelength of the gas being analyzed for. Another filter may also be used as a reference filter at a wavelength close to but not overlapping any of the gases present in the sample cell.

In processing the signals typically developed in the foregoing described type of gas analyzer, it is necessary to perform gating or switching in order to process and demodulate the resulting pulsed signal. This gating or switching typically requires accurate phase coherence of the gating or synchronizing signal with the pulses of the input or detected signal. In order to accomplish this, many prior art systems and techniques employ electro-mechanical or electro-optical means to produce phase related timing signals. This typically necessitates the employment of a separate detection system with accompanying electronics, increasing the cost and complexity of the system.

It is an object of the present invention to provide an improved gas analyzer and gas analyzing method wherein a series of synchronizing pulses are developed related to a series of detected pulses.

Another object of the invention is to provide an improved method and improved apparatus for developing synchronizing pulses in an infrared gas analyzer or the like.

A further object of the invention is to provide a gas analyzer and gas analyzing method wherein a series of synchronizing pulses are developed related to a series of input pulses provided by a rotary filter wheel without the necessity of employing separate electromechanical or electro-optical detectors for the filter wheel.

Other objects of the invention will become apparent to those skilled in the art from the following description, taken in connection with the accompanying drawings wherein.

Figure 1:
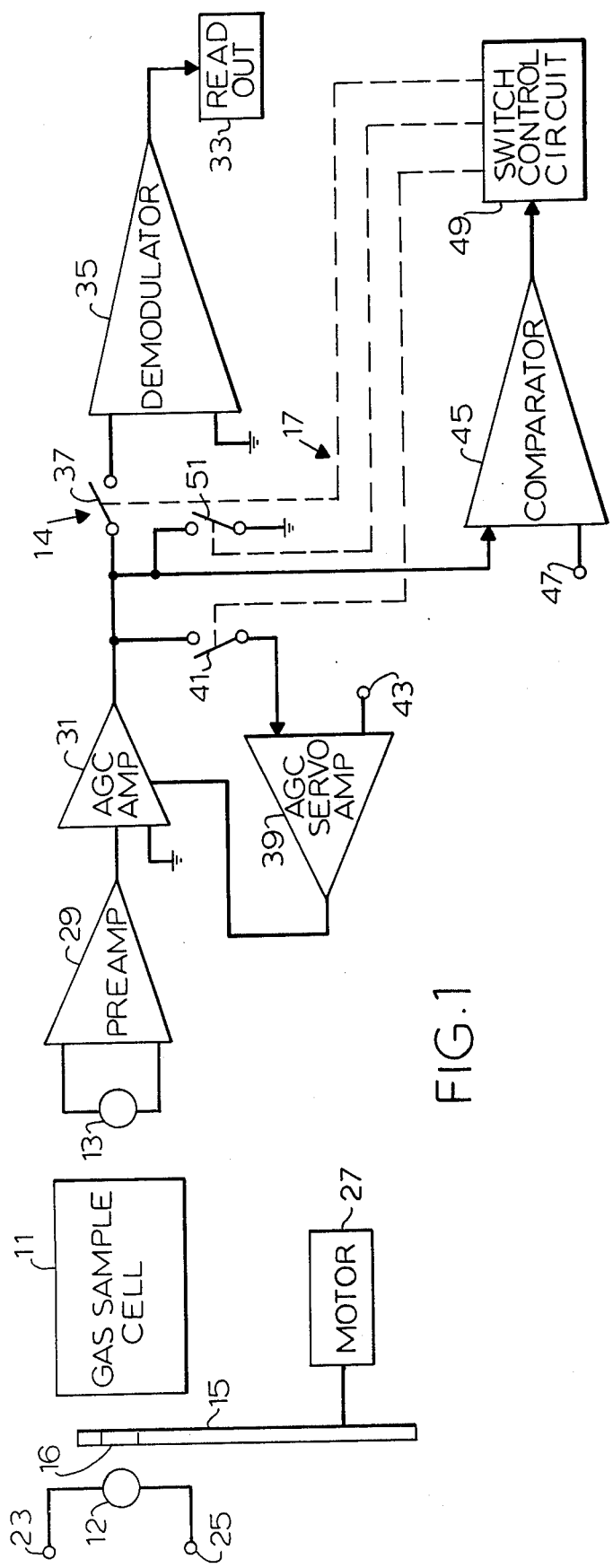
FIG. 1 is a block diagram of an infrared non-dispersive gas analyzer incorporating the invention.

Very generally, the gas analyzer of the invention comprises a sample cell 11 for containing the gas mixture to be analyzed. Means 12 produce and direct infrared energy through the sample cell, and the infrared energy passing through the sample cell is detected by a detector 13. A rotary filter wheel 15 successively and repetitively positions at least one filter 16 in the path of the infrared energy. The electrical signal representing the detected infrared energy is processed by suitable electronic processing means 14 which produce an output indicating the concentration of the constituents of the gas in the sample cell. Synchronizing means 17 are connected to the electrical signal processing means 14 for providing synchronizing pulses thereto. The synchronizing means 17 are coupled to the detecting means 13 and are responsive to the electrical signal produced by the detecting means to produce the synchronizing pulses.

Referring now more particularly to FIG. 1, a simplified block diagram of a non-dispersive infrared gas analyzer is illustrated. The gas analyzer includes an infrared source 12 of suitable design connected across a pair of terminals 23 and 25. Infrared energy from the source 12 is transmitted through the gas sample cell 11 to the detector 13. A rotary filter wheel 15 is positioned partially in the path of the infrared beam between the source 12 and the detector 13. The wheel 15 is rotated by a suitable motor 27 to periodically interpose one or more filters in the path of the infrared energy passing through the gas sample cell 11. As is known in the art, these filters correspond to the wavelength of the absorption characteristic of the gas or gases being analyzed for, passing energy only at that wavelength. A reference filter may also be used unrelated to any of the gases present.

Signals from the detector 13 are passed by a preamplifier 29 to the input of an automatic gain controlled amplifier 31. The automatic gain controlled amplifier 31, which is part of the signal processing electronics 14, cooperates therein to develop the information desired from the gas analyzer. The signal processing electronics 14 may be digital or analog in design and the information developed thereby is passed to a suitable readout system, display, or processor 33.

Depending upon the particular design of the signal processing electronics 14, the timing requirements will vary. Thus, if more than one gas is being analyzed for, several different series of timing signals may be required. Examples of such circuitry may be found in the aforementioned U.S. patents and in other patents relating to gas analyzers. For purposes of illustration, however, a specific form of the processing electronics 14 is illustrated in FIG. 1 and is described herein. In its broadest sense, however, the invention is applicable to many forms of signal processing circuitry which utilize synchronizing signals timed in relation to the position of the filter wheel 15.

The signal processing electronics 14 require phase information related to the phase of the pulses produced by rotation of the filter wheel 15. Such phase information can be derived from the wheel by suitable electro-mechanical or electro-optical systems. Such systems, however, are typically expensive and add complexity to the apparatus, which may be undesirable. Moreover, such systems frequently require stabilization of temperature and isolation against vibration, which add further complications.

The present invention utilizes the detector output signals directly to derive phase information for the signal processing electronics 14. Thus, electromechanical or electro-optical devices related to the filter wheel 15 are not required. More specifically, the AGC amplifier 31 is connected to the input of the demodulator 35 through a switch 37. The output of the demodulator 35 drives the readout system 33. The gain of the automatic gain controlled amplifier 31 is controlled by a servo-loop comprising an automatic gain control servo-amplifier 39 having one input connected through a switch 41 to the output of the amplifier 31 and having the other input connected to a reference voltage 43.

The synchronizing means 17 include a comparator 45, one input of which is connected to the output of the automatic gain controlled amplifier 31 and the other input of which is connected to a reference voltage 47. The output of the comparator is connected to a switch control circuit 49 which is operable to control the switches 37 and 41, and a further switch 51, at preselected timed intervals, as will be explained. The switch 51, when closed, clamps the output of the automatic gain controlled amplifier 31 to ground. The switches may be individual field effect transistors or a functionally similar chip, reed switches, or any other suitable switches.

Figure 2:
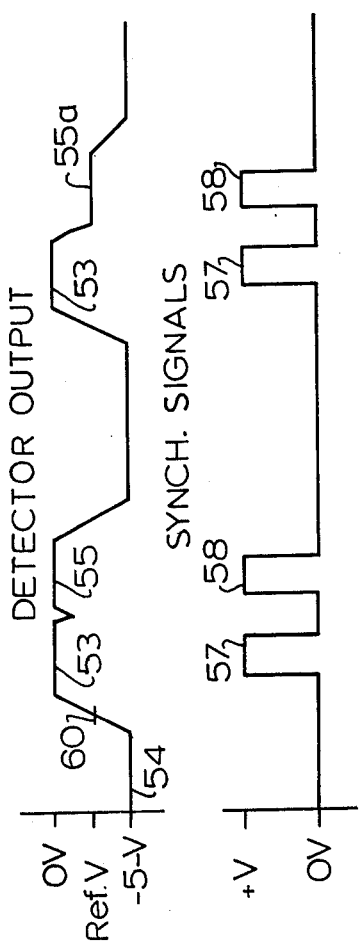
FIG. 2 is a graph illustrating two waveforms produced by the apparatus of FIG. 1.

Referring now to FIG. 2, the operation of the apparatus of FIG. 1 may be more readily understood. One type of waveform which may be produced by the automatic gain controlled amplifier 31 is shown in the uppermost curve in FIG. 2. The first portion of the curve represents a pair of contiguous pulses produced by two immediately adjacent filters on the rotating filter wheel 15. The first one of the two contiguous pulses is indicated at 53 and comprises a rising portion as the first filter moves into the infrared path, and a flat portion representing the period of time during which the first filter is fully interposed in the infrared path. The particular pair of composite or contiguous pulses illustrated occur when a second filter is positioned immediately adjacent the first filter on the filter wheel 16. The second filter produces a pulse indicated at 55 and there is a slight notch between the two pulses representing the transition period from one filter to the other. The flat top portion of the pulse 55 represents the period of time during which the second filter is fully interposed in the optical path. The declining portion represents that period of time during which the second filter is passing out of the optical path.

The second pair of contiguous pulses in FIG. 2 represents the situation where there is a specific gas corresponding to the second filter present in the gas sample cell 11 of FIG. 2. In this condition, the first pulse 53, which represents the reference signal, will be substantially identical with the pulse 53 in the left-hand portion of the curve of FIG. 2. However, the second pulse, indicated by the pulse 55a, is attenuated by the amount of absorption at that wavelength resulting from the presence of the corresponding gas in the sample cell. The difference in amplitude between the reference pulse 53 and the pulse 55a represents the concentration of the gas corresponding to the pulse 55a in the sample cell 11.

In the specific system illustrated in FIG. 1, the amount of attenuation is determined by sampling the pulses at specific times. The synchronizing signals for accomplishing this are indicated in the lower curve of FIG. 2. It may be seen that, for accuracy, the synchronizing pulses, which are square-wave in form, are less in width than the constant amplitude portions of the pulses 53, 55, and 55a, and are timed so as to occur precisely in the constant amplitude sections of those pulses. The switch control circuit 49 operates the switches 41, 51 and 37 at appropriate times in order to accomplish this. The beginning of the sequencing of the synchronizing pulses may be initiated by the leading edge, trailing edge, or any other suitable portion of the detector output pulses.

By properly operating the switches, that portion of the optical or detected infrared signal appearing in the optical path at a particular wavelength is summed into the demodulator 35. A decrease in the pulse as represented by the pulse 55a because of absorption will be demodulated and averaged by the demodulator 35. The resultant d-c signal at the output of the demodulator will be proportional to the absorption and to the gas concentration in the sample cell 11. The switch 51 serves to clamp the portion of the reference pulse or pulse 53 during the period of the first synchronizing signals 57 to ground. With the reference portion of the signal clamped to ground, the switch 41 activates the servo-loop causing the servo amplifier 39 to adjust the background signal level to −5 volts, as indicated by the lower portion of the curve 54 in FIG. 2. Thus, the system is span stabilized in that the reference amplitude is constant.

Figure 3:
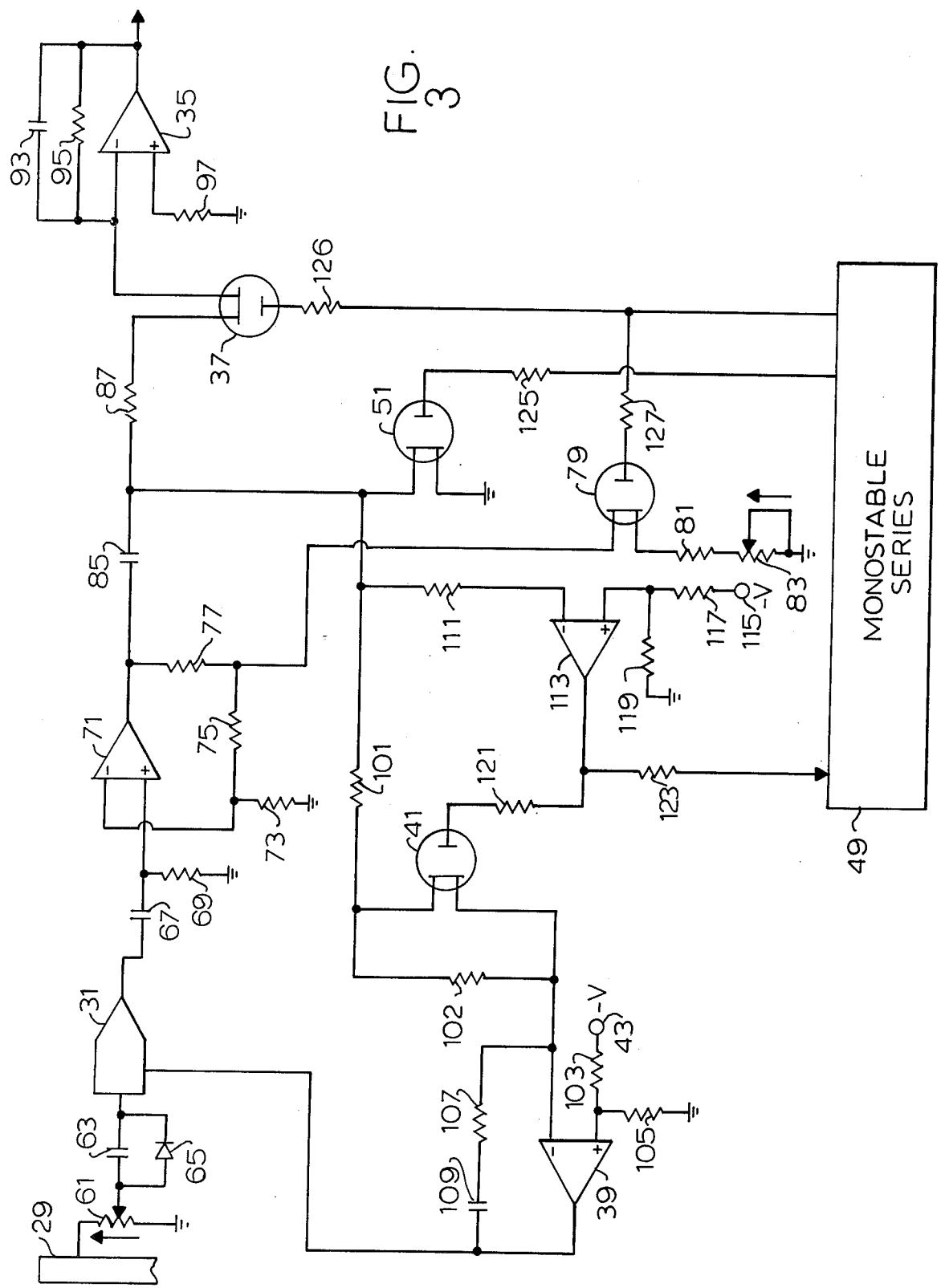
FIG. 3 is a schematic diagram more specifically illustrating one particular embodiment of the invention.

Referring now to FIG. 3, a more specific form of the signal processing electronics 14 and synchronizing electronics 17 is depicted. Input from the preamplifier 29 is applied to the automatic gain controlled amplifier 31 through a variable gain adjusting resistor 61 and suitable coupling capacitor 63. Diode 65 is connected in parallel with capacitor 63, to prevent a reverse bias voltage on the capacitor when the system is initially powered up. The output of the amplifier 31 is applied through a capacitor 67 and across a load resistor 69 to the positive input of an operational amplifier 71. The negative input of the amplifier 71 is connected to ground through a resistor 73 and is also connected through a pair of resistors 75 and 77 to the output of the operational amplifier 71. The junction between the resistors 75 and 77 is connected to ground through a field effect transistor switch 79, a fixed resistor 81, and a variable resistor 83 for calibration adjustment. The output of the operational amplifier 71 is connected through a capacitor 85 and series resistor 87 to the negative input of the operational amplifier 35 by means of a field effect transistor switch 37. A capacitor 93 and a resistor 95 are connected across the amplifier 35. The positive output of the amplifier 35 is grounded through a resistor 97. The junction between the capacitor 85 and the resistor 87 is connected to ground through a field effect transistor switch 51.

The junction between the capacitor 85 and the resistor 87 is also connected through a series resistor 101 and a field effect transistor switch 41 to the negative input of the automatic gain control servo amplifier 39. The reference voltage terminal 43 is connected through a resistor 103 to the positive input across a load resistor 105. A resistor 107 and a series capacitor 109 are connected across the amplifier 39. The output of the amplifier 39 is connected to the gain controlled amplifier 31 for servoing the gain thereof.

The junction between the capacitor 85 and the resistor 87 is also connected through a series resistor 111 to the negative input of a comparator 113. A reference voltage 115 is applied through a resistor 117 across a load resistor 119 to the positive input of the amplifier 113. The output of the amplifier 113 is connected to the base of the field effect transistor 41 by a series resistor 121 and is also connected through a series resistor 123 to a series of monostables which comprise the switch control circuit 49. The monostables may be of any suitable construction as is known in the art to trigger square wave pulses at precise intervals from the time of receiving an input signal. In this particular instance, two output pulses are provided by the monostables 49. The first of these pulses is applied through a resistor 125 to the base of the field effect transistor 51. The second of these pulses is provided through a resistor 126 to the base of the field effect transistor 79. The first of these pulses constitutes the pulse 57 in the lower waveform of FIG. 2, and the second of these pulses constitutes the pulse 58 or 58a of the same waveform.

In the illustrated circuit of FIG. 3, the electronics recognize the first reading edge of the signal output of the detector, indicated in the uppermost waveform of FIG. 2. All timing and generation of the synchronizing signals are derived from that leading edge, rendering the optical or infrared signal produced by the detector 13 of FIG. 1 self-synchronous. In operation, the amplifier 31 has a gain which is a function of the d-c voltage applied thereto from the amplifier 39. The output of the amplifier 31 is connected to the input of the amplifier 71, which provides a substantially high gain, for example, approximately 25. The amplifier 35 serves as a demodulator, integrator, or averager and meter driver. The comparator 113 is used to recognize the leading edge of the signal present at the output of the amplifier 71 at the junction between the capacitor 85 and the resistor 87. The threshold level, determined by the reference voltage, causes the amplifier 113 to change logic state when the waveform (FIG. 2) goes more positive then the reference level 60 (FIG. 2). The output from the amplifier 113 then triggers the monostable series 49, causing the logic signals indicated in the lower curve of FIG. 2. During the logic signal pulse 57, the field effect transistor switch 51 clamps the signal at the junction between the resistor 87 and the capacitor 85 to ground. During the synchronizing pulse 58, the field effect transistor switch 37 samples the second pulse 55 or 55a, applying it to the amplifier 35 or demodulator.

The output of the amplifier 113 also directly drives a field effect transistor switch 41 which allows the signal at the junction between capacitor 85 and the resistor 87 to be summed into the negative or inverting input of the AGC servo amplifier 39. This servo-loop, which is connected to the gain control of the amplifier 31, adjusts the gain of the amplifier 31 such that the background portion of the signal will be −5 volts as shown in the upper curve of FIG. 2. Moreover, the delayed pulse 57 from the monostable series causes the field effect transistor 51 to clamp the junction between the capacitor 85 and the resistor 87 to ground and thereby function as a d-c restorer. Thus, with the reference portion of the signal clamped at ground and the background level servoed to a constant negative voltage, the system is span stabilized.

The second synchronizing pulse 58 (FIG. 2) operates the field effect transistor switch 37, summing into the operational amplifier 35 that portion of the pulse output of the detector of the desired wavelength appearing in the analytical path. The pulse output 58 also serves to trigger the field effect transistor 79, for providing a gain adjustment with resistor 83 which serves to electronically equalize the top of the pulse waveform in FIG. 2. This is used to compensate for any initial optical unbalance as a result of unequal filter transmission.

It may be seen, therefore, that the apparatus of the invention, and the method employed thereby constitute an improved method and apparatus for gas analysis whereby the synchronizing of the processing electronics requires no external pickups at the rotary filter wheel. Rather, synchronization is accomplished by suitable processing of the detected signal.

Various modifications of the invention in addition to those shown and described herein will become apparent to those skilled in the art from the foregoing description and accompanying drawings. Such modifications are intended to fall within the scope of the appended claims.

What is claimed is:

1. A method for producing synchronizing pulses in a gas analyzer having a sample cell for containing a gas mixture to be analyzed, means for producing and directing infrared energy through the sample cell, means for detecting the infrared energy passing through the sample cell and producing an electrical signal representative thereof, means coupled to the detecting means for processing the electrical signal to produce an output indicating the concentration of the constituents of the gas in the sample cell, and a rotary filter wheel for successively and repetitively positioning at least one filter in the path of the infrared energy, said method comprising detecting a preselected rising or falling portion of said electrical signal representative of the infrared energy, and developing the synchronizing signals at a fixed time relationship to said rising or falling portion.

2. A method according to claim 1 wherein the filter wheel contains two substantially adjacent filters such that corresponding pulses produced are substantially contiguous, and wherein a pair of synchronizing pulses are produced at preselected times following a preselected amplitude of the rising portion of the first of said contiguous pulses, one during the first of said contiguous pulses and the other during the second of said contiguous pulses.

3. A method according to claim 2 wherein said pair of synchronizing pulses are each of a width substantially less than the width of each of said contiguous pulses.

4. In a gas analyzer comprising a sample cell for containing gas to be analyzed, means for producing and directing infrared energy through said sample cell, means for detecting the infrared energy passing through said sample cell and producing an electrical signal representative thereof, means coupled to said detecting means for processing the electrical signal to produce an output indicating the concentration of the constituents of the gas in said sample cell, and a rotary filter wheel for successively and repetitively positioning at least one filter in the path of the infrared energy, the improvement which comprises means for detecting a preselected rising or falling portion of said electrical signal representative of the infrared energy, and means for developing synchronizing signals at a fixed time relationship to said rising or falling portion and applying said synchronizing signals to said processing means.

5. The apparatus of claim 4 wherein said filter wheel contains two substantially adjacent filters such that corresponding pulses produced are substantially contiguous, and wherein said means for developing the synchronizing signals include means for producing a pair of synchronizing pulses at preselected times following a preselected amplitude of the rising portion of the first of said contiguous pulses, one during the first of said contiguous pulses and the other during the second of said contiguous pulses.

6. Apparatus according to claim 5 wherein said synchronizing signal developing means are adapted to provide pulses which are each of a width substantially less than the width of each of said contiguous pulses.

7. A gas analyzer comprising, a sample cell for containing gas to be analyzed, means for producing and directing infrared energy through said sample cell, means for detecting the infrared energy passing through said sample cell and producing an electrical signal representative thereof, means coupled to said detecting means for processing the electrical signal to produce an output indicating the concentration of the constituents of the gas mixture in said sample cell, a rotary filter wheel for successively and repetitively positioning at least one filter in the path of the infrared energy, and synchronizing means connected to said electrical signal processing means for providing synchronizing pulses thereto, said synchronizing means being coupled to said detecting means and being responsive to the electrical signal produced thereby to produce the synchronizing pulses.

8. A gas analyzer according to claim 7 wherein said processing means comprise gain controlled amplifier means for amplifying the electrical signal produced by said detecting means, means for adjusting the gain of said gain controlled amplifier means to produce a preselected amplitude level output, means for clamping the output of said gain controlled amplifier means to ground, demodulator means for producing an output representative of the gas concentration, and switch means responsive to said synchronizing means for controlling the time during which said gain adjusting means, said clamping means, and said demodulator means are operable to thereby produce a span stabilized phase sensitive demodulator output.

9. A gas analyzer comprising, a sample cell for containing a gas mixture to be analyzed, means for producing and directing infrared energy through said sample cell, means for detecting the infrared energy passing through the sample cell and producing an electrical signal representative thereof, a rotary filter wheel for successively and repetitively positioning at least a pair of filters in the path of the infrared energy, gain controlled amplifier means coupled to the output of said detecting means, demodulator means coupled to the output of said gain controlled amplifier means for providing an output signal representing the concentration of the constituents of the gas in said sample cell, an automatic gain control servo-loop coupling the output of said gain controlled amplifier means back thereto for controlling the gain thereof, comparator means coupled to the output of said gain controlled amplifier means and operable to provide a controlling output when the amplitude of the output of said gain controlled amplifier means exceeds a predetermined level, switch control means connected to the output of said comparator means for providing switch control signals in a preselected time sequence, first switch means for controlling said automatic gain controlled servo-loop and operable by said switch control means, second switch means coupled to the output of said gain controlled amplifier means for clamping same to ground in response to signals applied thereto by said switch control means, and third switch means connected between the output of said gain controlled amplifier means and said demodulator means and responsive to signals applied thereto from said switch control means, whereby suitable sequencing of said first, second, and third switch means provides a span stabilized phase sensitive demodulated signal.

* * * * *